United States Patent
Sugahara

[11] Patent Number: 6,117,523
[45] Date of Patent: *Sep. 12, 2000

[54] ABSORBENT ARTICLE WITH COMFORTABLE AND RAPID ACQUISITION TOPSHEET

[75] Inventor: Kazuko Sugahara, Osaka, Japan

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/744,892

[22] Filed: Nov. 8, 1996

Related U.S. Application Data

[63] Continuation of application No. 08/232,242, filed as application No. PCT/US92/09718, Nov. 6, 1992.

[30] Foreign Application Priority Data

Nov. 11, 1991 [JP] Japan ................................. 3-110211
Sep. 21, 1992 [JP] Japan ................................. 4-251718

[51] Int. Cl.⁷ ............................... B32B 3/14; A61F 13/15

[52] U.S. Cl. .......................... 428/134; 428/136; 428/137; 428/138; 428/190; 442/394; 604/385.1; 604/385.2

[58] Field of Search ................................. 428/131, 134, 428/136, 137, 138, 189, 190; 604/385.1, 385.2; 442/394

[56] References Cited

U.S. PATENT DOCUMENTS

| | | |
|---|---|---|
| 2,295,439 | 9/1942 | Voigtman . |
| 2,564,689 | 8/1951 | Harwood et al. . |
| 2,900,980 | 8/1959 | Harwood . |

(List continued on next page.)

FOREIGN PATENT DOCUMENTS

| | | |
|---|---|---|
| 0 040 084 | 11/1981 | European Pat. Off. . |
| 0 088 738 A1 | 9/1983 | European Pat. Off. . |
| 0165807 | 12/1985 | European Pat. Off. . |
| 0 272 683 A2 | 6/1988 | European Pat. Off. . |
| 0 321 985 A2 | 6/1989 | European Pat. Off. . |
| 0 329 160 A2 | 8/1989 | European Pat. Off. . |
| 0 335 252 A2 | 10/1989 | European Pat. Off. . |
| 0 347 746 A1 | 12/1989 | European Pat. Off. . |
| 0 358 031 A3 | 3/1990 | European Pat. Off. . |
| 0471114 | 2/1992 | European Pat. Off. . |
| 0 523683 A1 | 1/1993 | European Pat. Off. . |
| 3038535 | 3/1982 | Germany . |
| 3037032 A1 | 5/1982 | Germany . |
| 1-122727 | 8/1989 | Japan . |
| 845826 | 8/1960 | United Kingdom . |
| 2 124 907 | 2/1984 | United Kingdom . |
| 2135892 | 9/1984 | United Kingdom . |
| 2214085 | 8/1989 | United Kingdom . |
| 9014813 | 12/1990 | WIPO . |

OTHER PUBLICATIONS

U.S. application No. 08/706,115, Van Tilburg, filed Aug. 30, 1996.

*Primary Examiner*—Elizabeth M. Cole
*Attorney, Agent, or Firm*—Kevin D. Bogg; Edward J. Milbrada

[57] ABSTRACT

An absorbent article such as a sanitary napkin, having an improved topsheet that provides improved skin comfort as well as superior fluid handling characteristics. Such absorbent articles comprise a main body portion preferably comprising a liquid pervious topsheet, a liquid impervious backsheet, and an absorbent core positioned between the topsheet and the backsheet. The main body portion has longitudinal edges and lateral edges. The topsheet has a central zone and a pair of end zones extending laterally outwardly from and contiguous with the central zone. The topsheet comprises a nonwoven outer layer and an apertured thermoplastic film layer. The nonwoven outer layer has an opening positioned in the central zone. The apertured thermoplastic film layer is positoned beneath the nonwoven outer layer so that the apertured thermoplastic film layer and the nonwoven outer layer covers the end zones while the apertured thermoplastic film layer is exposed through the opening of the nonwoven outer layer in the central zone.

14 Claims, 7 Drawing Sheets

U.S. PATENT DOCUMENTS

| | | |
|---|---|---|
| 3,676,242 | 7/1972 | Prentice . |
| 3,888,254 | 6/1975 | Hendricks . |
| 3,927,673 | 12/1975 | Taylor . |
| 3,929,135 | 12/1975 | Thompson . |
| 3,945,386 | 3/1976 | Anczurowski et al. . |
| 3,965,906 | 6/1976 | Karami . |
| 3,967,623 | 7/1976 | Butterworth et al. . |
| 3,994,299 | 11/1976 | Karami . |
| 4,014,341 | 3/1977 | Karami . |
| 4,285,342 | 8/1981 | Mesek . |
| 4,321,924 | 3/1982 | Ahr . |
| 4,323,069 | 4/1982 | Ahr et al. . |
| 4,324,246 | 4/1982 | Mullane et al. . |
| 4,333,465 | 6/1982 | Wiegner . |
| 4,340,563 | 7/1982 | Appel et al. . |
| 4,397,644 | 8/1983 | Matthews et al. . |
| 4,480,000 | 10/1984 | Watanabe et al. . |
| 4,519,799 | 5/1985 | Sakurai et al. . |
| 4,578,066 | 3/1986 | O'Connor . |
| 4,662,877 | 5/1987 | Williams ............... 604/385 A |
| 4,675,013 | 6/1987 | Ruffo . |
| 4,690,679 | 9/1987 | Mattingly, III et al. . |
| 4,710,186 | 12/1987 | DeRossett et al. . |
| 4,725,473 | 2/1988 | Van Gompel et al. . |
| 4,755,413 | 7/1988 | Morris . |
| 4,762,520 | 8/1988 | Wallstrom . |
| 4,781,962 | 11/1988 | Zamarr et al. ............... 428/138 |
| 4,795,454 | 1/1989 | Dragoo . |
| 4,798,603 | 1/1989 | Meyer et al. . |
| 4,798,604 | 1/1989 | Carter . |
| 4,806,411 | 2/1989 | Mattingly, III et al. . |
| 4,878,974 | 11/1989 | Kagawa . |
| 4,908,026 | 3/1990 | Sukiennik et al. . |
| 5,019,062 | 5/1991 | Ryan et al. . |
| 5,023,124 | 6/1991 | Kobayashi . |
| 5,134,007 | 7/1992 | Reising et al. . |
| 5,330,598 | 7/1994 | Erdman et al ............... 156/164 |
| 5,415,640 | 5/1995 | Kirby et al. . |
| B1 4,589,876 | 4/1993 | Van Tilburg . |

ABSORBENT ARTICLE WITH COMFORTABLE AND RAPID ACQUISITION TOPSHEET

This is a continuation of application Ser. No. 08/232,242, filed on Aug. 29, 1994, which is a 371 of PCT/US92/09718, filed Nov. 6, 1992.

FIELD OF THE INVENTION

The present invention relates to absorbent articles such as sanitary napkins, adult incontinence pads, and the like. Still more particularly, the present invention concerns an improved topsheet providing excellent skin comfort and fluid acquisition.

BACKGROUND OF THE INVENTION

All manner and variety of absorbent articles configured for the absorption of body fluids such as menses, urine, and feces are, of course, well known. Generally, absorbent articles comprise a liquid pervious topsheet, a liquid impervious backsheet, and an absorbent core positioned between the topsheet and the backsheet. The exudates from a wearer's body readily penetrate through the topsheet and are contained in the absorbent core.

The topsheet serves at least two purposes. First, the topsheet provides fluid handling properties including rapid aquisition of fluids through the topsheet and into the absorbent core and the prevention of "re-wet" of those fluids absorbed by the absorbent core, that is, fluids once absorbed into the absorbent core will not leak back through the topsheet to wet the wearer's skin. Second, the topsheet provides skin comfort by being compliant, soft feeling, dry, and non-irritating to the wearer's skin.

In order to provide better fluid handling characteristics and skin comfort, apertured thermoplastic films have been developed as a material for the topsheet. Apertured thermoplastic films have been preferred for the topsheet because they are pervious to liquids and yet non-absorbent. Thus, the surface of the apertured thermoplastic film which is in contact with the body remains dry and is more comfortable to the wearer. Such apertured thermoplastic films are available in the marketplace, and include films disclosed in U.S. Pat. No. 3,929,135, entitled "Absorptive Structure Having Tapered Capillaries", issued to Thompson on Dec. 30, 1975; U.S. Pat. No. 4,324,426, entitled "Disposable Absorbent Article Having A Stain-Resistant Topsheet", issued to Mullane and Smith on Apr. 13, 1982; U.S. Pat. No. 4,342,314, entitled "Resilient Plastic Web Exhibiting Fiber-Like Properties", issued to Radel and Thompson on Aug. 3, 1982; and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984, all of which are herein incorporated by reference.

However, while apertured thermoplastic films provide excellent dryness and "re-wet" properties, further improvements in skin feel and comfort are desirable. In particular, some consumers have complained that the apertured thermoplastic films can feel hot, sweaty, or sticky.

Therefore, it is an object of the present invention to provide a topsheet having an improved skin comfort with superior fluid handling characteristics.

It is a further object of the present invention to provide an absorbent article with such an improved topsheet.

SUMMARY OF THE INVENTION

The present invention provides an absorbent article such as sanitary napkins, disposable diapers, incontinent pads, and the like, that have an improved topsheet that provides improved skin comfort as well as superior fluid handling characteristics. Such absorbent articles comprise a main body portion preferably comprising a liquid pervious topsheet, a liquid impervious backsheet, and an absorbent core positioned between the topsheet and the backsheet. The main body portion has longitudinal edges and lateral edges. The topsheet has a central zone and a pair of end zones extending laterally outwardly from and contiguous with the central zone. The topsheet comprises a nonwoven outer layer and an apertured thermoplastic film layer. The nonwoven outer layer has an opening positioned in the central zone. The apertured thermoplastic film layer is positoned beneath the nonwoven outer layer so that the apertured thermoplastic film layer and the nonwoven outer layer covers the end zones while the apertured thermoplastic film layer is exposed through the opening of the nonwoven outer layer in the central zone.

DETAILED DESCRIPTION OF THE INVENTION

Figure 1:
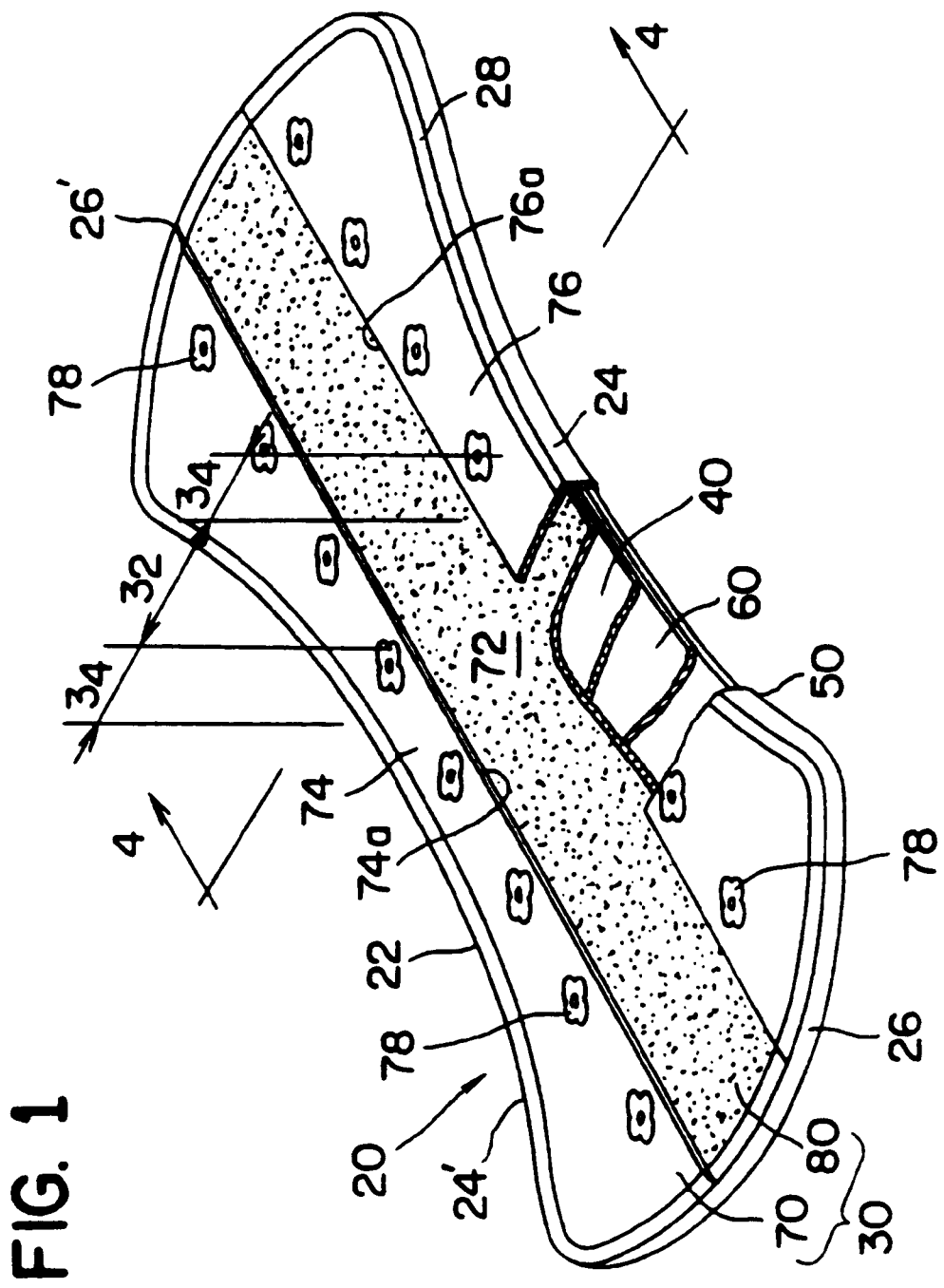
FIG. 1 is a perspective view of a pantiliner embodiment of the present invention having a portion cut away to reveal underlying structure.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). As used herein, the term "associated" encompasses configurations whereby a first member is directly joined to a second member and configurations whereby a first member is indirectly joined to a second member by affixing the first member to intermediate members which in turn are affixed to the second member. A preferred embodiment of an absorbent article of the present invention is the disposable absorbent article, pantiliner 20, shown in FIG. 1. As used herein, the terms "pantiliner", and "sanitary napkin" refers to absorbent articles generally worn by females adjacent to the pudendal region that are intended to absorb and contain the various exudates which are discharged from the body (e.g., blood, menses, and urine). The present invention, however, is not limited to the particular types or configurations of absorbent articles shown in the drawings. It should be understood that the present invention is also applicable to other absorbent articles such as incontinent pads, incontinent undergarments, diapers, and the like.

As shown in FIGS. 1–4, the pantiliner 20 comprises an absorbent means represented by main body portion 22. The main body portion 22 has longitudinal edges 24 and lateral edges 26. The term "longitudinal", as used herein, refers to a line, axis or direction in the plane of the pantiliner 20 that is generally aligned with (e.g., approximately parallel to) a vertical plane which bisects a standing wearer into left and right body halves when the pantiliner 20 is worn. The term "lateral" as used herein, refers to a line, axis or direction which lies within the plane of the pantiliner 20 that is generally perpendicular to the longitudinal direction.

The main body portion 22 comprises a topsheet 30, a backsheet 50, and an absorbent core 60. The main body portion 22 also preferably comprises a nonwoven secondary layer 40.

The topsheet 30 is liquid permeable and when the pantiliner 20 is in use, the topsheet 30 is compliant, soft feeling, and non-irritating to the user's skin. The topsheet 30 has a central zone 32 and a pair of end zones 34. The end zones 34 extend laterally from and are contiguous with the central zone 32.

The topsheet 30 comprises a nonwoven outer layer 70 and an apertured thermoplastic film layer 80. The nonwoven outer layer 70 is liquid permeable and has an opening 72 positioned in the central zone 32. The opening 72 is provided in the nonwoven outer layer 70 as a passageway for body exudates to be deposited directly onto the apertured thermoplastic film layer 80 to take advantage of its superior fluid handling properties so that fluid will rapidly pass into the absorbent core. In a preferred embodiment, the nonwoven outer layer 70 comprises two strips 74, 76. The two strips 74, 76 of the nonwoven outer layer 70 are spaced apart on top of the apertured thermoplastic film layer 80 so that the spaced region between the two strips 74, 76 forms the opening 72. In this particular embodiment, each strip 74, 76 has approximately parallel inner edges 74a, 76a being separated apart from the lateral edge 26 to the other lateral edge 26 whereby the opening 72 has a substantially rectangular shape elongated in the longitudinal direction.

So long as the opening 72 in the center (longitudinally) of the central zone 32 is sufficiently large to permit the flow of body fluids intended to be absorbed by the core, this longitudinal ends of the central zone 32 can be covered with the nonwoven outer layer 70 or a separate layer (not shown).

The nonwoven outer layer 40 extends lateraly into the seam around the periphery 28 of the main body portion 22. The seam bonds together the nonwoven outer layer 70, the apertured thermoplastic film layer 80, and optionally the nonwoven secondary layer 40 by a securement means. The preferred pantiliner 20 has concave longitudinal edges 24,24 to fit to the contour of the wearer's panty. In this embodiment, the nonwoven outer layer 70 has a width of at least about 1.5 mm in both end zones at the narrowest portion and about at least 7–10 mm at the widest portion. The width of the opening will depend upon the intended use of the article. For low-flow pantiliners the width of the opening is greater than about 5 mm, preferably about 10 mm to 30 mm, greater preferably about 20 mm. For heavier-flow sanitary napkins, the width of the opening is more than about 10 mm, preferably about 20–60 mm, more preferably about 40 mm. The ratio of the width of the opening 72 to the total lateral width of the main body portion can vary based on the width of the nonwoven outer layer 40. The ratio is preferably about 4:1 to about 1:4, more preferably from about 2:1 to 1:2. It has been found that such shapes and area for the opening 72 is desirable from a product performance, process, and aesthetics standpoint. However, other shapes and various areas are possible in the design of the opening 72. For example, each strip 74, 76 can have a non-parallel inner edge, or can meet at or inward from either or both longitudinal edges 26, 26' to define a circular opening. So long as the opening 72 is sufficiently large to permit passage of most of the fluids deposited onto the topsheet in the opening to pass, the particular arrangement or configuration of the opening is not critical.

The nonwoven outer layer 70 is preferably secured in at least partial contacting relation with the apertured thermoplastic film layer 80. The nonwoven outer layer 70 can be maintained in contact with the apertured thermoplastic film layer 80 by fusion bonding, adhesive attachment of the layers, or by any other securement means. The bonding of the nonwoven outer layer 70 to the apertured thermoplastic film layer 80 can prevent the nonwoven outer layer from being torn or from rolling back onto itself at edges 74a, 76a, thereby importing an uncomfortable feeling. Fusion bonding includes heat bonding, ultrasonic bonding, and the like. Heat bonding is the preferred means for securing the nonwoven outer layer 70 and the apertured thermoplastic film layer 80 in contacting relation. The two layers can be continuously, partially, or intermittently bonded together. In a preferred embodiment, the nonwoven outer layer 70 and the apertured thermoplastic film layer 80 are spot-bonded at a plurality of positions along the inner edge 74a, 76a of each strip 74, 76 with a heat bond 78. The heat bonds 78 provide an embossed seal pattern that can also convey an aesthetic effect in its pattern design such as a flower, a leaf, and so on.

The nonwoven outer layer provides softness in the end zones of the topsheet in order to eliminate any problems of a sticky, sweaty feeling for the user as well as a member that can efficiently handle any liquids deposited onto the end zones. The nonwoven outer layer 70 comprises a nonwoven web having excellent flexibility compliance and fluid aquisition. A suitable material for use as the nonwoven outer layer 70 of the topsheet comprises mixtures of polyethylene (the melting point is relatively low temperature), polypropylene, and/or polyester, known in the art as a "bi-component web". A layer adjacent to one surface of the nonwoven web comprises mainly bi-component fibers (preferably 50/50 by weight) of polyethylene and polypropylene. A layer adjacent to the other surface comprises mainly bi-component fibers (also preferably 50/50 by weight) of polyethylene and polyester. Nonwoven webs comprising fibers containing polyethylene are particularly suitable for use in the present invention because they can be readily fusion bonded. The fusion bonding between the nonwoven web and the apertured thermoplastic film layer are performed by melting of the polyethylene in the fibers. Both of the above layers contain the polyethylene in the fibers so that either layer can be arranged to face toward the apertured thermoplastic film layer for fusion bonding. Preferably, the layer of the nonwoven web comprising the bi-component fibers of polyethylene and polyester is arranged to face toward the apertured thermoplastic film layer 80. In this preferred arrangement, the layer of the nonwoven web comprising the bi-component fibers of polyethylene and polypropylene is arranged to face to the wearer, and provides superior flexibility compliance and soft feeing because of the character of the polypropylene. Further, the layer of the nonwoven web comprising the bi-component fibers of polyethylene and polyester perform a cushioning function. Exemplary nonwoven webs which can be used as the include the carded, nonapertured, through air bonded webs having a basis weight of about 21 grams/m$^2$ and comprising the layered structure of bicomponent fibers discussed above as are available from Fukumura Seishi Kabushiki kaisha, Gihu, Japan, under the designation S-2146. The nonwoven outer layer can also have a plane surface or embossed pattern, as designed by the manufacture of the article.

Figure 2:
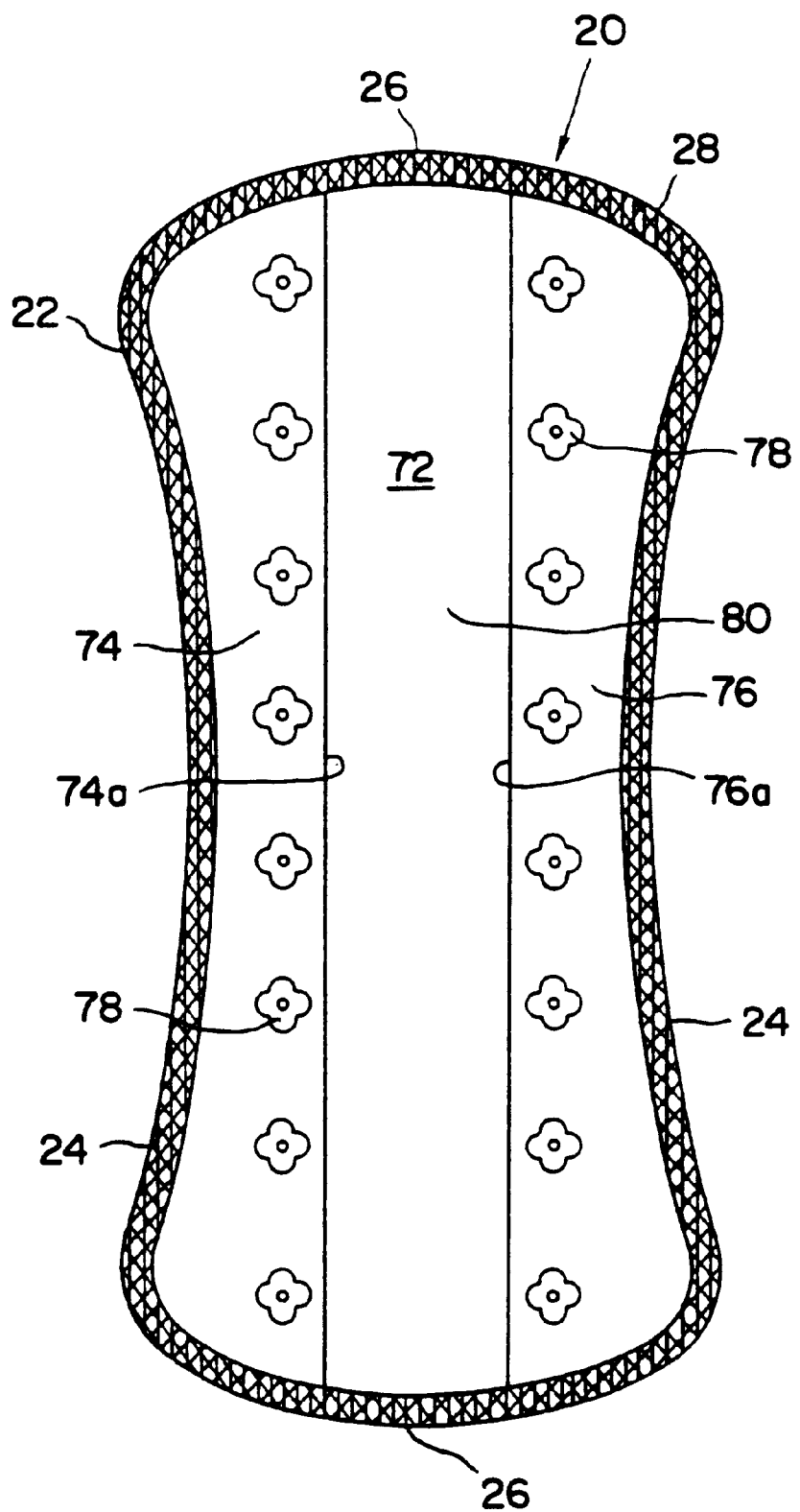
FIG. 2 is a top plan view of the pantiliner embodiment of the present invention shown in FIG. 1, the topsheet facing the viewer.
Figure 3:
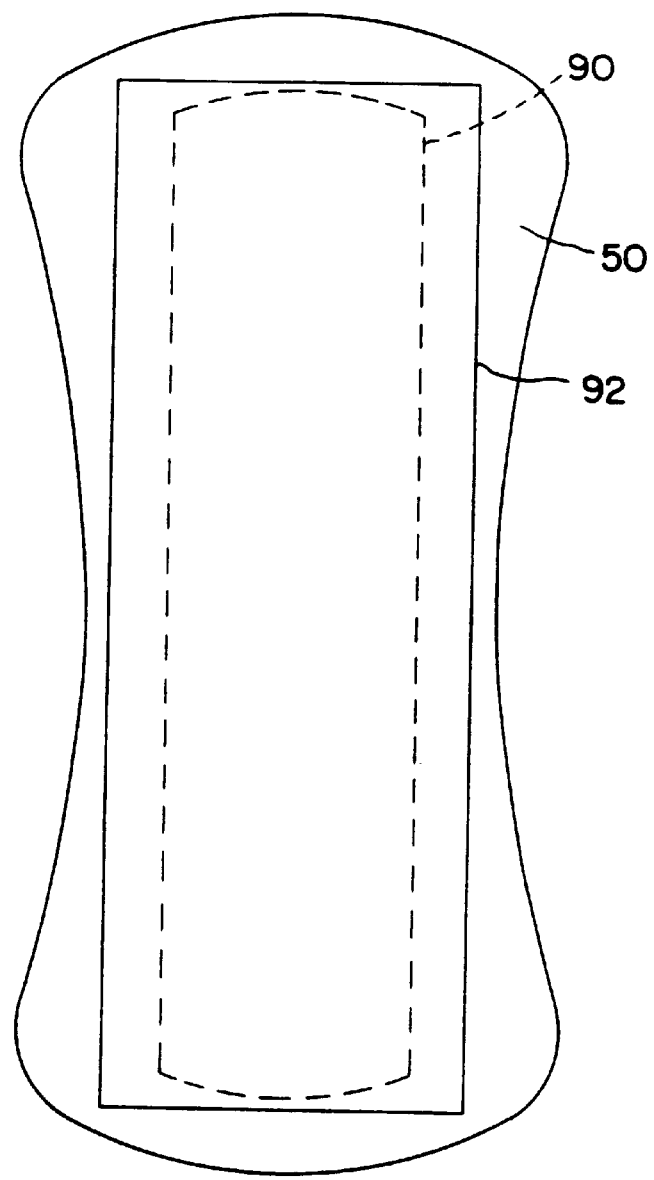
FIG. 3 is a bottom plan view of the pantiliner embodiment of the present invention shown in FIG. 1, the backsheet facing the viewer.

The apertured thermoplastic film layer 80 is liquid permeable and positioned beneath the nonwoven outer layer 70 and nearer to the absorbent core 60. The apertured thermoplastic film layer 80 and the nonwoven outer layer both overlay the end zones 34. Further, the apertured thermoplastic film layer 80 is exposed through the rectangular opening 72 of the nonwoven outer layer 70 in the central zone 32 from the lateral edge 26 to the other lateral edge 26. While the apertured thermoplastic film layer 80 need not extend to the lateral or longitudinal edges of the main body portion, in a preferred embodiment as shown in FIGS. 1 and 2, the apertured thermoplastic film layer 80 extends laterally and longitudinally outward and can form a portion of the longitudinal edges 24, 24' and lateral edges 26, 26' or the periphery 28.

Formed films are preferred for the apertured thermoplastic film layer because they are pervious to liquids and yet non-absorbent. Thus, the surface of the formed film which is in contact with the body remains dry and is more comfortable to the wearer. Suitable formed films for the apertured thermoplastic film are described in U.S. Pat. No. 3,929,135, entitled "Absorptive Structure Having Tapered Capillaries", issued to Thompson on Dec. 30, 1975, U.S. Pat. No. 4,324,426, entitled "Disposable Absorbent Article Having A Stain-Resistant Topsheet", issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimentional Plastic Web Exhibiting Non-Glossy Visible Surface and Cloth-Like Tactile Impression", issued to Ahr, Louis, Mullane, and Ouellette on Jul. 31, 1984. Each of these patents are incorporated herein by reference. A formed film which has been found to be satisfactory is manufactured by Tredegar Industries, Inc. of Terre Haute, Ind. under the designation X3265, and marketed as "Dri-Weave" on sanitary napkins produced by The Procter & Gamble Company of Cincinnati, Ohio.

In addition, in a preferred embodiment of the present invention, at least a portion of the outer surface (body-facing surface) 80a of the apertured thermoplastic film layer 80 is treated with a surfactant. It is preferred that the surfactant be substantially evenly and completely distributed at least in the central zone 32 of the outer surface 80a of the apertured thermoplastic film layer 80. This can be accomplished by any of the common techniques well known to those skilled in the art. For example, the surfactant can be applied to the apertured thermoplastic film layer 80 by spraying, by padding, or by the use of transfer rolls. Treating the outer surface 80a of the apertured thermoplastic film layer 80 with a surfactant renders the surface of the apertured thermoplastic film layer 80 more hydrophilic. This results in liquid penetrating the apertured thermoplastic film layer 80 faster than it would if the surface were not so treated. This diminishes the likelihood that menstrual fluids will flow off the apertured thermoplastic film layer 80 rather than being absorbed by the absorbent core 60.

In a particularly preferred embodiment, an additional nonwoven secondary layer 40 is positioned between the absorbent core 60 and the apertured thermoplastic film layer 80. The nonwoven secondary layer 40 prevents "bunching", that is, twisting of pantiliner per se, or of the absorbent core in the crotch portion which twisting can leakage of body exudates, and provides additional softness at the periphery 28 of the main body portion. The inner surface 80b of the apertured thermoplastic film layer 80 is preferably secured in contacting relation with the nonwoven secondary layer 40. This contacting relationship results in liquid penetrating the apertured thermoplastic film layer 80 faster than if the apertured thermoplastic layer 80 were not in contact with the nonwoven secondary layer 40. The apertured thermoplastic film layer 80 can be maintained in contact with the nonwoven secondary layer 40 by, for example, heat sealing as described herein above, or by applying adhesive to the inner surface 80b of the apertured thermoplastic film layer 80. Preferably, the contacting relationship is applied by the same type of securement means as that between the nonwoven outer layer 70 and the apertured thermoplastic layer 80, more preferably, the same spot-bonding and heat sealing.

The nonwoven secondary layer 40 is liquid permeable and positioned between the apertured thermoplastic film layer 80 and the absorbent core 60. In one particular embodiment, the nonwoven secondary layer 40 is extended laterally and longitudinally outward and forms a portion of the longitudinal edges 24, 24' and lateral edges 26, 26' of the periphery 28. The material of the nonwoven secondary layer 40 can be the same as the nonwoven outer layer 70. Preferably, the surface of the nonwoven web comprising the mixture of polyethylene and polyester fibers arranged to face towards the apertured thermoplastic film layer 80 for securement by fusion bonding in a contact relationship. In this particular embodiment, the surface 40b of the nonwoven secondary layer 40 facing the absorbent core 60 secured in contacting relation with the absorbent core 60. The contacting relationship can be achieved by the same securement means described above for maintaining the contacting relationship between the apertured thermoplastic film layer 80 and the nonwoven secondary layer 40. Preferably, the contacting relationship is achieved by applying the adhesive to face between the nonwoven secondary layer 40 and the absorbent core 60. Suitable adhesives useful for this purpose are described in U.S. Pat. No. 4,917,697, and which is incorporated herein by reference. The adhesives can be applied by the same methods as described above for the surfactant applied to the outer surface 80a of the apertured thermoplastic film layer 80. The absorbent core 60 can be secured to the nonwoven secondary layer 40 by a uniform continuous layer of adhesive, a patterned layer of adhesive, or an array of separate lines, spirals, or spots of adhesive. An exemplary adhesive is manufactured by Findley Adhesives Company of Wauwatosa, Wis. and designated as H-2128. The securement means between the apertured thermoplastic film layer 80 and the nonwoven secondary layer 40 will preferably comprise an open pattern network of filaments of adhesive as is disclosed in U.S. Pat. No. 4,573,986 entitled "Disposable Waste-Containment Garment", issued to Minetola and Tucker on Mar. 4, 1986, and which is incorporated herein by reference. An exemplary securement means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference.

The absorbent core 60 is positioned between the topsheet 30 and the backsheet 50. In one particular embodiment, the absorbent core 60 extends longitudinally and laterally such that the edges of the absorbent core 60 form a portion of the longitudinal edges 24, 24' and lateral edges 26, 26' of the main body portion 22. The absorbent core 60 provides the means for absorbing menstrual fluid. The absorbent core 60 need not have an absorbent capacity much greater than the total amount of menstrual fluid anticipated to be absorbed. The absorbent core 60 is generally compressible, comformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer absorbent gelling materials, peat moss, or any equivalent material or combinations of materials. An exemplary absorbent core is a tissue layer such as is manufactured by Ft. Howard and designated as grade 882. The absorbent core may also have a layer of absorbent gelling material, such as in the form of particles, disposed between two air-laid tissue layers (or "upper" and "lower" tissue layers). The first and second tissue layers provide containment of the absorbent gelling material, improved lateral wicking of the absorbed exudates throughout the absorbent core, and a degree of absorbency. Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Aquisition Zones", issued to Alemany et al. on May 30, 1989; and European Patent Application No. 0 198 683, the Procter & Gamble Company, published Oct. 22, 1986 in the name of Duenk, et al. Each of these patents are incorporated herein by reference.

Absorbent gelling materials mentioned above are those materials which, upon contact with fluids (i.e., liquids) such as water or body fluids, imbibe such fluids and thereby form hydrogels. In this manner, fluids discharged into the absorbent core 60 can be acquired and held by the absorbent gelling materials, thereby providing the articles herein with enhanced absorbent capacity and/or improved fluid retention performance. Preferred absorbent gelling materials which are employed in the absorbent core 60 will generally comprise particles of a substantially water-insoluble, slightly cross-linked, preferably neutralized, hydrogel-forming polymer material. The term "particles", as used herein, can refer to particles in any form, such as in the form of pellets, flakes, or fibers. The characteristics of the absorbent core 60 (including, but not limited to preferred types of polymer materials used herein, and types of methods which can be used for preparing these polymer particles) are described in greater detail in U.S. Pat. No. 5,009,653 issued to Osborn which is all incorporated by reference herein.

The backsheet 50 is impervious to liquids and is preferably manufactured from a thin plastic film, although other flexible liquid pervious materials may also be used. As used herein, the term "flexible" refers to materials which are compliant and will readily conform to the general shape and contours of the human body. Further, the backsheet 50 may permit vapors to escape from the absorbent core 60 (i.e., breathable) while still preventing liquid exudates from passing there through. The size of the backsheet 50 is generally dictated by the size of the absorbent core 60. In a preferred embodiment, the backsheet 50 extends laterally and longitudinally to form a portion of the longitudinal edges 24, 24' and lateral edges 26, 26' of the periphery 28 of the main body portion 22. Any material used in the art for such purpose can be utilized herein. An exemplary film for use as the backsheet is manufactured by Tredeger Industries, Inc, of Terre Haute, Ind. under the designation X8297. The backsheet 50 is preferably embossed and/or matte finished to provide a more clothlike appearance. Preferably, the backsheet is a thermoplastic film having a thickness of from about 0.012 mm (0.5 mil) to about 0.051 mm (2.0 mils).

The backsheet 50 is preferably secured to the absorbent core 60 by securement means (not shown) such as those well known in the art. Suitable securement means are the same means hereinbefore disclosed with respect to securing the nonwoven secondary layer 40 to the absorbent core 60.

The main body portion 22 described above can be relatively thick or relatively narrow and thin. A narrow main body portion 22 can be effective because the overall configuration and use of the pantiliner 20 (or sanitary napkin) results in the main body portion 22 being maintained in close proximity to the body. Such proximity of the main body portion 22 places it precisely where it should be: very near the body at the vaginal opening. The main body portion 22 can then absorb the vast majority of the menstrual fluid (menses) before it has an opportunity to flow along the sides of the main body portion 22. A thin main body portion can also be desired because it is typically comfortable to the user.

The main body portion 22 further preferably comprises an adhesive attachment means for securing the main body portion 22 in the crotch portion of a panty. The outer surface 50a of the backsheet 50, adjacent the central region in a longitudinal direction, is preferably coated with an adhesive 90. The pantiliner 20 can be maintained in position by attaching the adhesive to the undergarment.

The fastener used with the present invention is not limited to an adhesive attachment means. Any type of fastener used in the art can be used for such purpose. For example, the pantiliner 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990, which patent is incorporated herein by reference. For simplicity, however, the fastener will be described in terms of an adhesive attachment means. A suitable adhesive is manufactured by H. B. Fuller Company of St. Paul, Minn. and designated as HL-2254.

The adhesive attachment means is respectively covered by a removable release liner, preferably a central pad release liner which is designated 92. The adhesives should be covered with a release liner to keep the adhesives from sticking to extraneous surfaces prior to use. A suitable release liner is described in U.S. Pat. No. 4,917,697 entitled "Sanitary Napkin Having Flaps and Stress Relief Means", issued to Osborn, Ill., et al. on Apr. 17, 1990, which patent is incorporated herein by reference. Another exemplary release liner is the release paper manufactured by Akrosil Corporation, and designated as BL25 MGA, Silox 4R/0.

Figure 4:
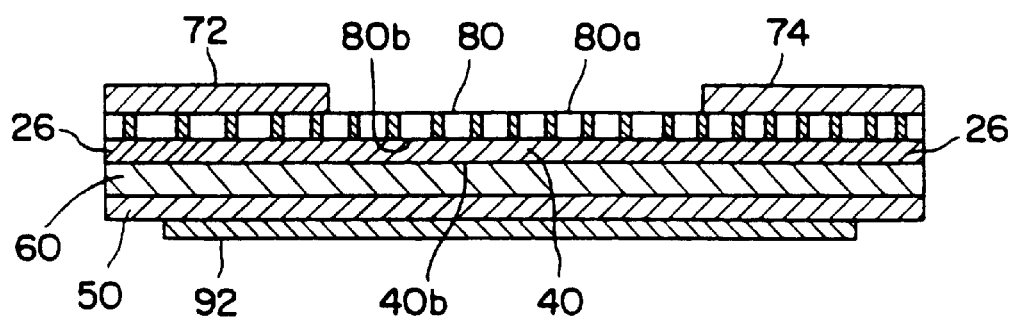
FIG. 4 is an enlarged lateral cross-sectional view taken along line 4—4 of FIG. 1.

In an alternative embodiment of the present invention, the nonwoven outer layer 70 and the nonwoven secondary layer 40 can be made of the same piece of material. A nonwoven web is laid down beneath the apertured thermoplastic film layer 80 to form the nonwoven secondary layer 40. The nonwoven web is then c-folded about the longitudinal edges of the apertured thermoplastic film layer 80 so as to cover the end zones of the apertured thermoplastic film layer 80 and form the nonwoven outer layer 70. Heat bonding can be done to the above mentioned portion, (i.e., the periphery 28) at a plurality of positions 78 along the inner edges of strip. The nonwoven secondary layer 40 is attached, for example, by glue to the absorbent core 60. The periphery of the component assembled as described above is then cut along the outer edges to form the pantiliner, thereby providing a periphery 28 which comprises portions thereof consisting of the topsheet 30 layers, the nonwoven secondary layer 40, the absorbent core 60, and the backsheet 50, as shown in FIG. 4.

Furthermore, the longitudinal edges 24 and lateral edges 26, of the periphery 28 is formed with all soft material such as the nonwoven outer layer 60, the nonwoven secondary layer 40, the absorbent core 60, so that the periphery is relatively thick so that the periphery is more comfortable and soft to the wearer's skin. Similar soft edges are disclosed in the U.S. Pat. No. 4,752,349 herein incorporated by reference.

Figure 5:
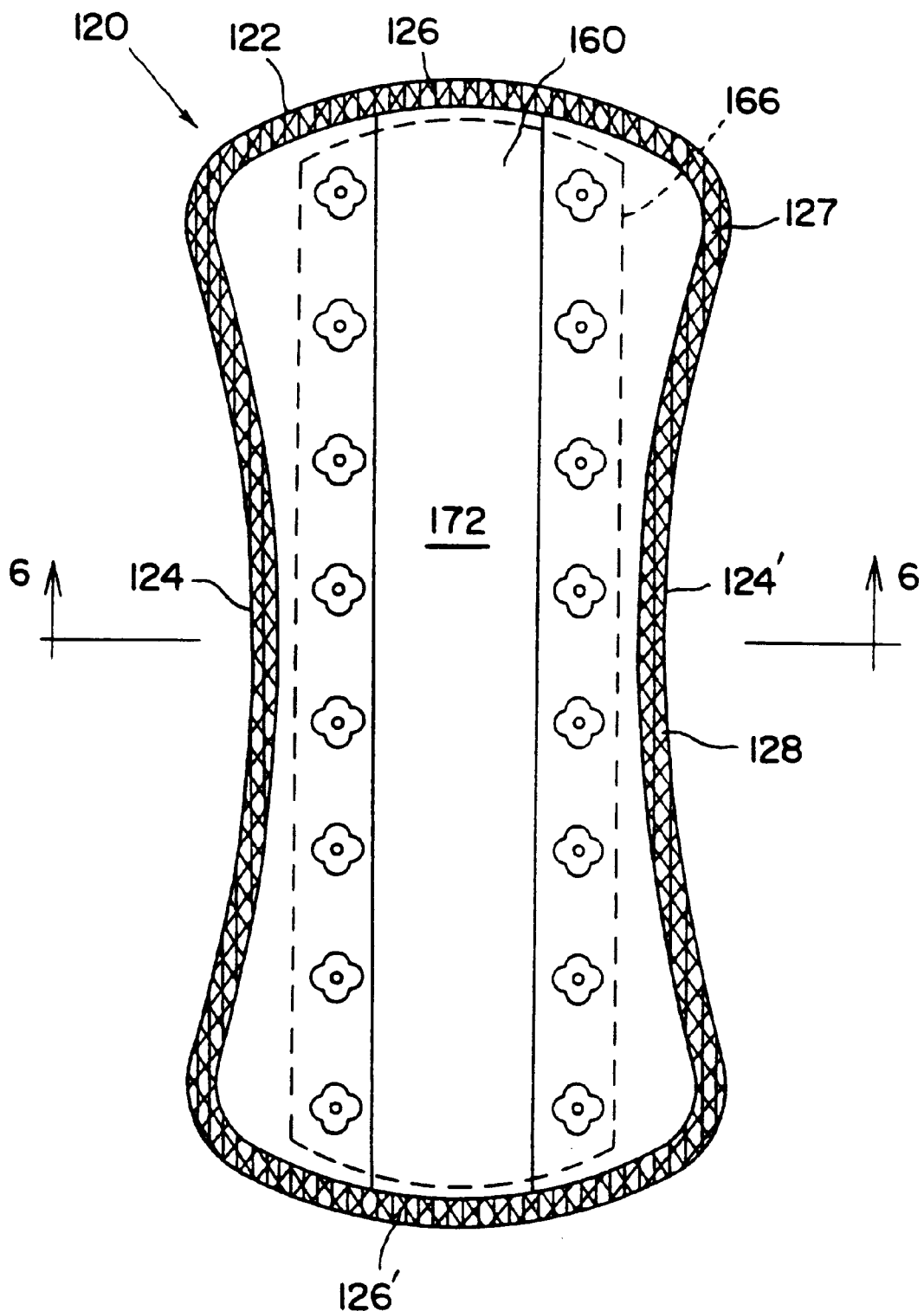
FIG. 5 is a top plan view of an alternative pantiliner embodiment of the present invention.
Figure 6:
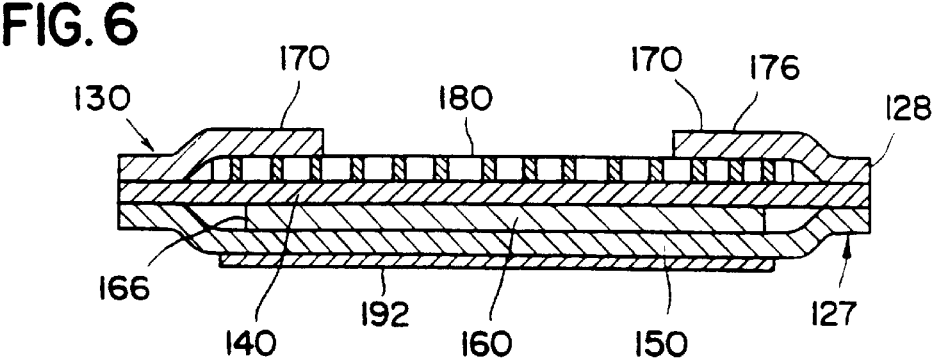
FIG. 6 is an enlarged lateral cross-sectional view taken along line 6—6 of FIG. 5.

FIGS. 5–6 show an alternative embodiment of the present invention, wherein the absorbent core 160 and the apertured thermoplastic film layer 180 are at least laterally coextensive. The widths of the absorbent core and the apertured thermoplastic film layer can be selected as needed for different product uses or designs. For example, in a sanitary napkin involving heavy flow; the absorbent core 160 can be slightly larger than the apertured thermoplastic film layer 180 in a plan view. This pantiliner 120 also comprises an absorbent means represented by main body portion 122 substantially like the pantiliner 20 described above, except as hereinafter described. In this particular embodiment, the nonwoven outer layer 170, any optional nonwoven secondary layer 140, and the backsheet 150 extend outwardly and are bonded together to form the seam 127 at the periphery 128 of the main body portion by fusion bonding, adhesive, or any other securement means. Thereby, the periphery 166 of the absorbent core 160 (shown by dashed line in FIG. 5) is not positioned in the periphery seam 127.

Figure 7:
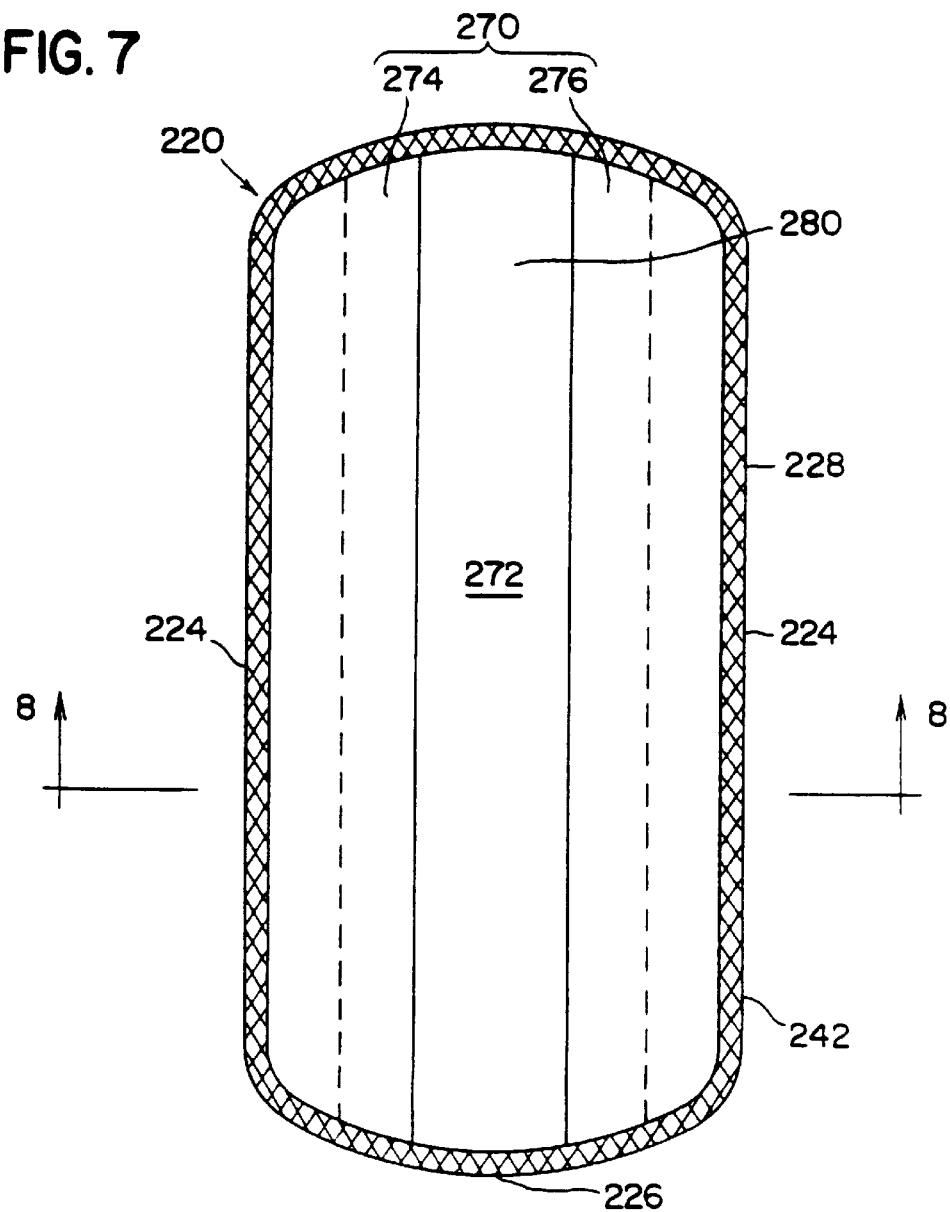
FIG. 7 is a plan view of a further alternative sanitary napkin embodiment of the present invention.
Figure 8:
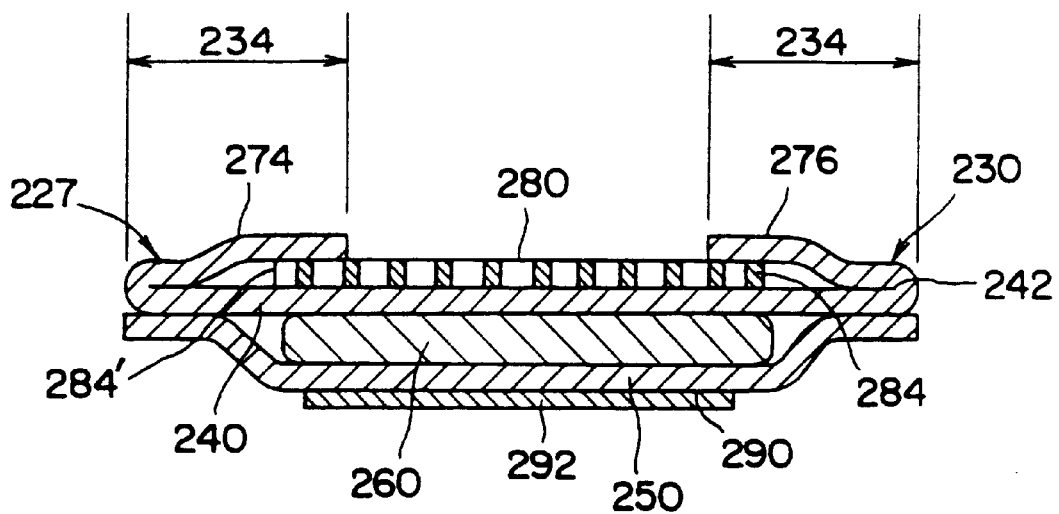
FIG. 8 is an enlarged lateral cross-sectional view taken along line 8—8 of FIG. 7.

FIGS. 7–8 show a further alternative embodiment of the present invention of a sanitary napkin 220 wherein the nonwoven outer layer 270 and the nonwoven secondary layer 240 consist of a single piece of nonwoven web such that the nonwoven web is c-folded about the longitudinal ends 284, 284' of the apertured thermoplastic film layer 280 in the end zones 234. In this particular embodiment, there is a distance provided between the longitudinal edges 284, 284' of the apertured thermoplastic film layer 280 and folded line 242 of the nonwoven web. The unitary nonwoven outer layer 270, the nonwoven secondary layer 240, and the backsheet 250 are extended outwardly and form a seam 227 at the periphery 228.

The absorbent core 260 is secured in contacting relation between the nonwoven secondary layer 240 and the backsheet 250. In this particular embodiment, the absorbent core 260 and the apertured thermoplastic film layer 280 are at least laterally coextensive. The absorbent core 260 is preferably relatively thick to contain large amount of body exudates. Optionally, a portion of the periphery 228 of the main body portion 222 can be trimmed off.

Figure 9:
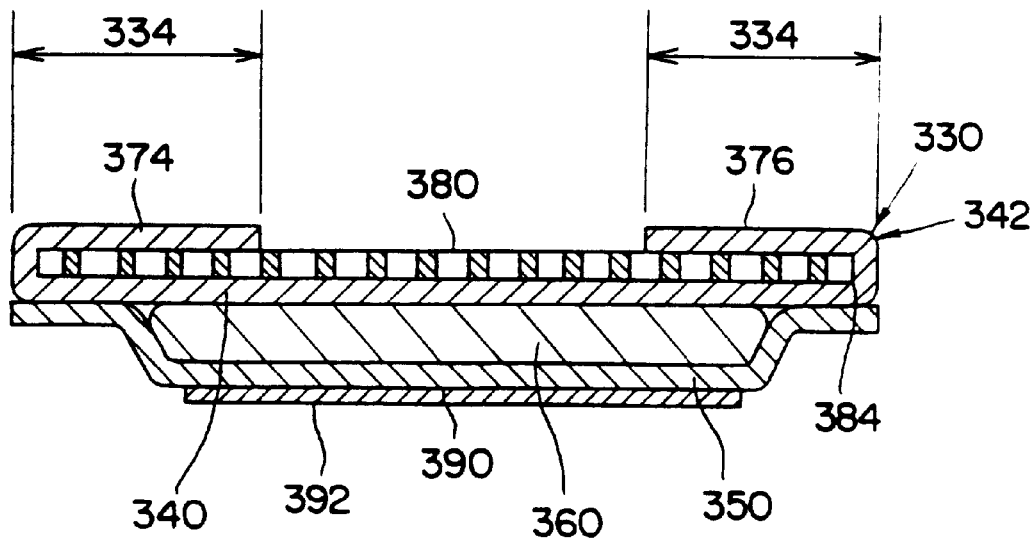
FIG. 9 is an enlarged lateral cross-sectional view of a still further alternative sanitary napkin embodiment of the present invention.

FIG. 9 shows a further embodiment of the present invention, wherein sanitary napkin 320 is similar to sanitary napkin 220, except that the longitudinal edges 384 of the apertured thermoplastic film layer 380 extend to the folded line 342 of the nonwoven web.

The pantiliners or sanitary napkins disclosed hereinbefore can additionally comprise a pair of flaps. Each flap is associated with the main body portion at a line of juncture and extends laterally outward from the longitudinal edges of the main body portion. The flaps can comprise separate pieces of material which are attached to the main body portion. In preferred embodiments, such as those shown in U.S. Pat. No. 4,917,697 issued to Osborn, the flaps may be unitary with at least one member of the main body portion.

Figure 10:
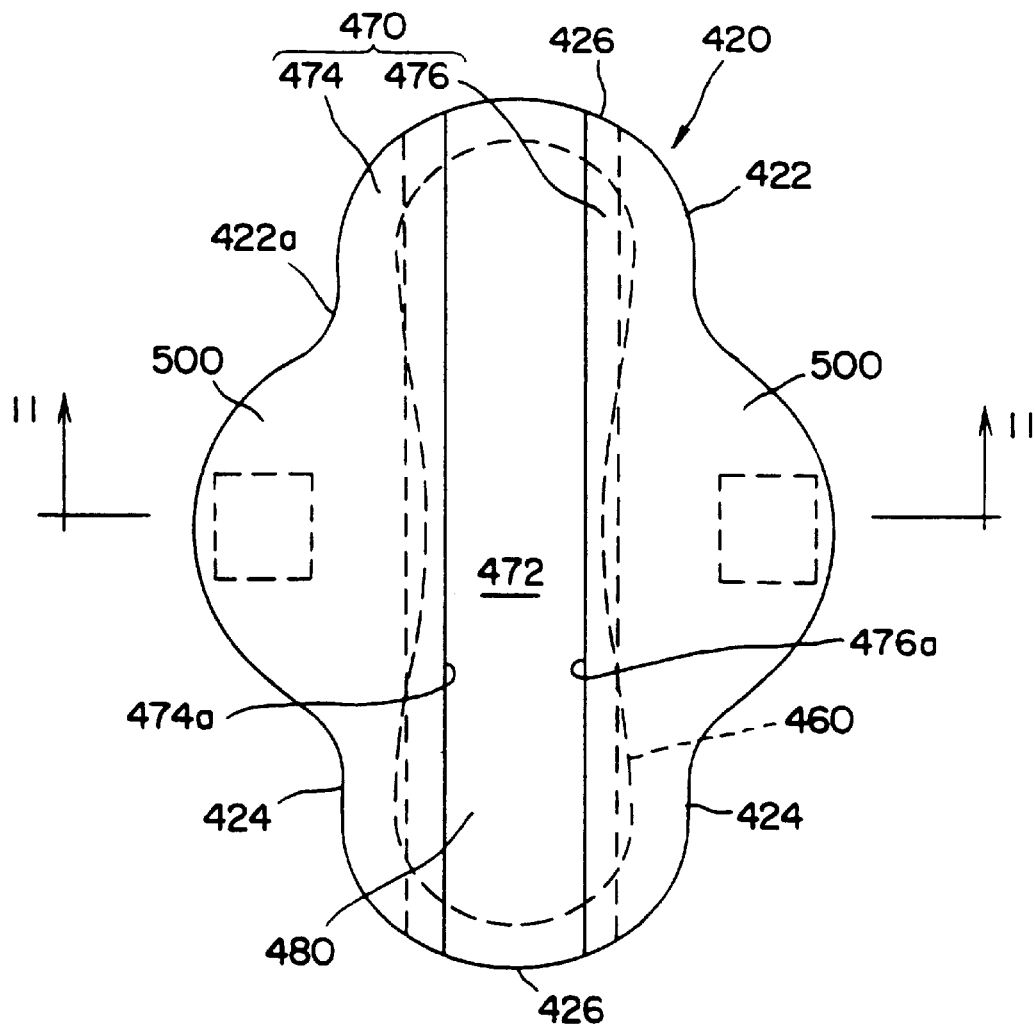
FIG. 10 is a yet another alternative pantiliner embodiment of the present invention additionally comprising a pair of flaps.
Figure 11:
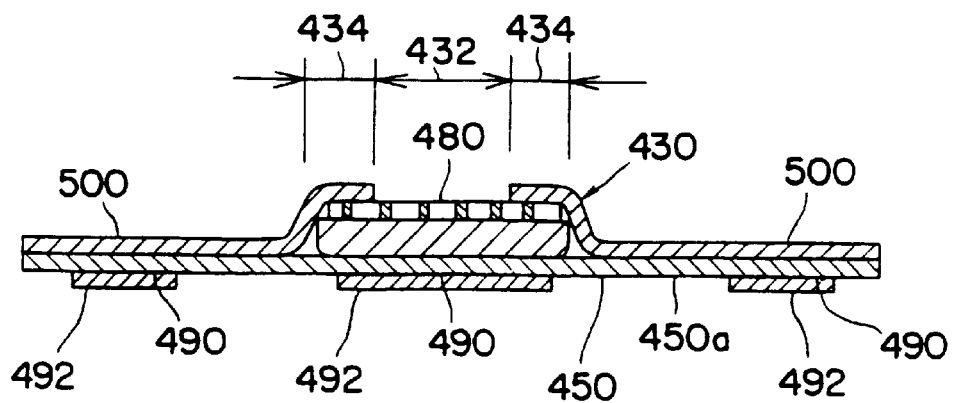
FIG. 11 is an enlarged lateral cross-sectional view taken along line 11—11 of FIG. 10.

FIGS. 10–11 show an embodiment of a pantiliner having a pair of flaps, each of which is adjacent to and extends laterally from the side edge of the absorbent core. The flaps are configured to fold over the edges of the wearer's panties. The flaps serve several purposes. First, the flaps help to prevent soiling of the wearer's body and panties by menstrual fluid by forming a double wall barrier at each side of the sanitary napkin, particularly when constructed of a liquid impervious material. Second, the flaps are preferably provided with attachment means on their garment surface so that the flaps can be folded back under the panty and attached to the garment facing side of the panty. In this way, the flaps serve to keep the sanitary napkin properly positioned in the panty. Third, the flaps can help to reduce bunching of the sanitary napkin, as such term is used in the above-referenced patent issued to Osborn. The flaps can be constructed of various materials including materials similar to the topsheet, backsheet, tissues, or combination of these materials. The flaps can be separate element(s) attached to the main body of the napkin, or can comprise extensions of the topsheet and backsheet (i.e., unitary). A number of sanitary napkins having flaps suitable or adaptable for use with the absorbent articles of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

As shown in FIGS. 10–11, the flaps 500 are each associated with the main body portion 422 along a line of juncture. The juncture is typically a longitudinally-oriented (or "longitudinal") juncture, such as lines of juncture 422a. As used herein, the terms "juncture" (or "line of juncture") refers to regions where the flaps extend from or are joined to the main body portion 422. These regions can be any of various curved or straight lines, but they are not limited to lines. Thus, these regions can comprise flanges, strips, intermittent lines, and the like. In the embodiment illustrated in FIG. 10, the line of juncture 422a is a relatively straight line.

In addition, the absorbent material of the sanitary napkin 420 may extend into the flaps to form a flap absorbent core, as described in greater detail in U.S. Pat. No. 4,917,697, or the flaps 500 can be a separate element attached to the main body portion. The flaps 500 can also comprise at least one of the materials forming the main body portion 422, (i.e., the nonwoven outer layer 470, the apertured thermoplastic film layer 480, the backsheet 450, the nonwoven secondary layer, or any additional materials.) In a preferred embodiment, the nonwoven outer layer 470, the apertured thermoplastic film layer 480, and the backsheet 450 are extended outwardly and form the seam 427 at a periphery 428 of the main body portion by fusion bonding, adhesive, or by any other securement means. Each strip 474, 476 of nonwoven outer layer 470 and the backsheet 450 are extended laterally and form the pair of flaps 500. The absorbent core 460 and the apertured thermoplastic film layer 480 are at least laterally coextensive. As shown in FIG. 10, it is preferable that the side edges of the absorbent core 460 and longitudinal edges of the apertured thermoplastic film layer 480 are not the same width.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a main body portion having a longitudinal centerline defining a longitudinal direction, a lateral centerline perpendicular to said longitudinal centerline defining a lateral direction, substantially longitudinally oriented edges and substantially laterally oriented edges, wherein said substantially longitudinally oriented edges and said substantially laterally oriented edges define a periphery for said main body portion and wherein at least one of said substantially laterally oriented edges is wider than the width of said main body portion at a location between said substantially laterally oriented edges, said main body portion comprising:
        a composite liquid pervious topsheet having a central zone and a pair of longitudinally oriented side zones each said side zone being positioned between said central zone and one of said longitudinal edges of said main body, said composite topsheet comprising:
        a) a nonapertured nonwoven outer layer which is able to acquire liquids deposited thereon, said nonwoven outer layer having a pair of longitudinally oriented inner edges in a predetermined spaced apart relationship wherein the lateral separation between said inner edges defines the lateral width of said central zone,
        b) an apertured thermoplastic film layer having longitudinal edges, said apertured thermoplastic film layer being positioned beneath said nonwoven outer layer so that said nonwoven outer layer overlies said apertured thermoplastic film layer in said side zones and said apertured thermoplastic film layer is exposed in at least a portion of said central zone, at least a portion of said thermoplastic film layer being treated with surfactant, wherein
        c) said nonwoven outer layer and said apertured thermoplastic film layer are joined by a pattern of intermittent fusion bonds;
    a liquid impervious backsheet associated with said topsheet; and
    an absorbent core having side edges, said absorbent core being positioned between said topsheet and said backsheet.

2. The absorbent article of claim 1 wherein said nonwoven outer layer comprises two strips spaced apart on top of said apertured thermoplastic film layer.

3. The absorbent article of claim 1 or 2 additionally comprising a nonwoven secondary layer positioned between said topsheet and said absorbent core, wherein said secondary layer is joined to both of said topsheet and said absorbent core.

4. The absorbent article of claim 3 wherein said nonwoven secondary layer and said nonwoven outer layer consist of a single piece of material c-folded around said longitudinal edges of said apertured thermoplastic film layer in each said side zone.

5. The absorbent article of claim 1 or 2 wherein said absorbent core is positioned below said central zone and said side zones.

6. The absorbent article of claim 1 or 2 wherein said side edges of said absorbent core form the longitudinal edges of said main body portion.

7. The absorbent article of claim 1 wherein said apertured thermoplastic film layer and said absorbent core are laterally coextensive.

8. The absorbent article of claim 1 or 2 additionally comprising a pair of flaps, each flap extending laterally outward beyond one of said longitudinal edges of said main body portion.

9. The absorbent article of claim 8 wherein each said flap comprises an extension of said nonwoven outer layer of said topsheet and an extension of said backsheet.

10. The absorbent article of claim 9 wherein said absorbent core and said apertured thermoplastic film layer are substantially laterally coextensive and positioned below said central zone and said side zones.

11. The absorbent article of claim 1 wherein the article is a pantiliner.

12. The absorbent article of claim 1 wherein the article is a sanitary napkin.

13. An absorbent article comprising:
    a main body portion having a longitudinal centerline defining a longitudinal direction, a lateral centerline perpendicular to said longitudinal centerline defining a lateral direction, substantially longitudinally oriented edges and substantially laterally oriented edges, wherein said substantially longitudinally oriented edges and said substantially laterally oriented edges define a periphery for said main body portion and wherein at least one of said substantially laterally oriented edges is wider than the width of said main body portion at a location between said substantially laterally oriented edges, said main body portion comprising:
        a liquid pervious composite topsheet having a central zone and a pair of longitudinally oriented side zones each said side zone being positioned between said central zone and one of said longitudinal edges of said main body, said composite topsheet comprising:
        a) a nonapertured nonwoven outer layer which is able to acquire liquids deposited thereon, said nonwoven outer layer comprising a bicomponent web and having a pair of longitudinally oriented inner edges in a predetermined spaced apart relationship wherein the lateral separation between said inner edges defines the lateral width of said central zone,
        b) an apertured thermoplastic film layer having longitudinal edges, said apertured thermoplastic film layer being positioned beneath said nonwoven outer layer so that said nonwoven outer layer overlies said apertured thermoplastic film layer in said side zones and said apertured thermoplastic film layer is exposed in at least a portion of said central zone, at least a portion of said thermoplastic film layer being treated with surfactant, wherein c) said nonwoven outer layer and said apertured thermoplastic film layer are joined by a pattern of intermittent fusion bonds;

a liquid impervious backsheet associated with said topsheet;

an absorbent core having side edges, said side edges extending outward such that said absorbent core is positioned between and joined to said topsheet and said backsheet about said periphery; and panty attachment means disposed on an outer surface of said backsheet in at least said central zone.

14. An absorbent article according to claim 13 wherein said absorbent article further comprises a secondary layer positioned between said absorbent core and said apertured thermoplastic film layer.

* * * * *